United States Patent [19]

Chinery

[11] Patent Number: 4,677,859
[45] Date of Patent: Jul. 7, 1987

[54] FLOW METER

[75] Inventor: David Chinery, Hayes, England

[73] Assignee: The British Petroleum Company, p.l.c., London, England

[21] Appl. No.: 757,469

[22] Filed: Jul. 22, 1985

[30] Foreign Application Priority Data

Aug. 4, 1984 [GB] United Kingdom ............... 8420882

[51] Int. Cl.$^4$ .............................................. G01F 1/78
[52] U.S. Cl. ................................................. 73/861.72
[58] Field of Search ..................................... 73/861.72

[56] References Cited

U.S. PATENT DOCUMENTS

| 1,401,299 | 12/1921 | Wohlenberg | 73/861.72 |
| 2,804,771 | 9/1957 | Brown | 73/861.72 |
| 2,897,672 | 8/1959 | Glasbrenner et al. | 73/861.72 |
| 3,203,241 | 8/1965 | Genthe | 73/861.72 |
| 3,429,181 | 2/1969 | Shiba | 73/861.72 |
| 3,538,769 | 11/1970 | Shiba | 73/861.72 |

FOREIGN PATENT DOCUMENTS 665990 2/1952 United Kingdom .

Primary Examiner—Herbert Goldstein
Attorney, Agent, or Firm—Morgan & Finnegan

[57] ABSTRACT

A flow meter suitable for the measurement of the mass flow rate of two phase flows. The flow meter has an S-shaped flow tube located within a housing. The housing has an inlet and outlet which are in register with the inlet and outlet of the flow tube. The flow tube has force transducers fitted at the bends of the tube which measure the reaction forces during fluid flow and enable a mass flow reading to be obtained.

8 Claims, 2 Drawing Figures

FLOW METER

The present invention relates to a flow meter and more particularly relates to a flow meter for measuring flow rates of single or multi phase fluids.

Flow meters are well known and are available in a number of forms such as mass flow meters, mechanical flow meters, vortex shedding meters etc. Most of these meters are unsuitable for the measurement of multiphase fluid flow without previous separation or homogenisation and the present invention relates to a novel flow meter capable of measuring the flow of single or multi phase fluids.

Thus according to the present invention there is provided a flow meter comprising a housing having an inlet and an outlet for fluid, a flow tube located within the housing and adapted to allow fluid flow from the inlet to the outlet, the flow tube being adapted to deflect the direction of fluid flow whereby reaction forces are generated on the flow tube and means for measuring the generated reaction forces.

The flow tube adapted to deflect the fluid flow direction may have a number of configurations. It is desirable that the flow tube has sufficient curvature so that all the components of the fluid flow impart force to the flow tube while changing the direction of flow. Preferably the flow tube has an S-bend geometry (most preferably having two 90° bends) in one plane. It is preferred that the total orientation change is from 90° to 180° and it is most preferred that the direction of flow is the same at the inlet and outlet of the housing. It is preferred that the bore of the flow tube is the same as that of the inlet and outlet of the housing and that they are co-axial.

It is preferred that the interior of the flow tube is in fluidic communication with the housing for example by the use of a narrrow circumferential gap or slot between the ends of the tube and the respective inlet or outlet. This arrangement allows rapid pressure equalisation between the interior of the tube and the housing which obviates the need for corrections of meter output during pressure variations occurring during multiphase flow, and the need for a pressure balancing system whilst allowing a flow meter construction having relatively few parts thereby promoting more reliability and ease of manufacture. The tube is preferably of a rigid construction and may be made from erosion and corrosion resistant materials such as ceramics, composites, metals etc.

The means for measuring the reaction force is preferably a force transducer or a load cell. It may be in the form of a strain gauge or piezo electric device. For a stable configuration it is desirable to use a tube having a pair of symmetrical bends there being a load cell arranged normal to each of the bends. The load cell is connected between the tube and the housing. The sum of the signals from the load cells is proportional to the couple generated by the change of fluid momentum. Combination of the signals with those from a velocity, density or other forms of sensor gives a continuous mass flow reading which may be processed as required.

For two phase gas-liquid flow it is necessary to measure the phase hold ups and phase velocities, or to known one phase velocity as a function of the other velocity, the phase holdup and flow regime. Measurement of phase holdup may be achieved, for example, by using either gamma ray densitometry or capacitance sensing. For densitometry the system required would be two gamma-ray sources mounted 90° apart on the outside pipe wall, and a scintillation counter mounted diametrically opposite each source and also on the outside of the pipe. The devices would be required to measure the complete 0-100% holdup range. Such equipment is commercially available.

The capacitance sensor is an alternative way of determining phase hold up, the principle of which is to measure the combined dielectric constant of the fluids in the pipe. This sensor has, however, to be mounted on electrically non-conducting pipe. Both of these methods provide a possible means of measuring the time dependent liquid holdup in a line.

Preferably the means for measuring the reaction force is located inside the housing. Preferably the tube has two or more rigid supports at least one of which has a means for measuring the reaction force. Most preferably each support has an associated means for mesuring the reaction force. These arrangements enable bearing friction effects to be reduced or eliminated and secondary parameters related to fluid/wall friction e.g. viscosity, may be inferred by differential measurement of the two output signals.

The invention will now be described by way of example only and with reference to the accompanying drawings.

Figure 1:
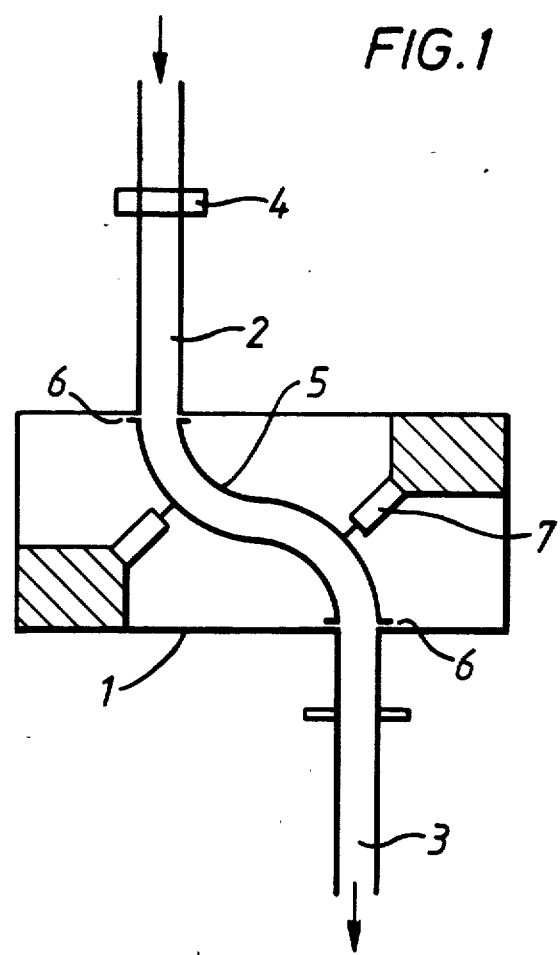
FIG. 1 shows a schematic diagram of a flow meter according to the invention.
Figure 2:
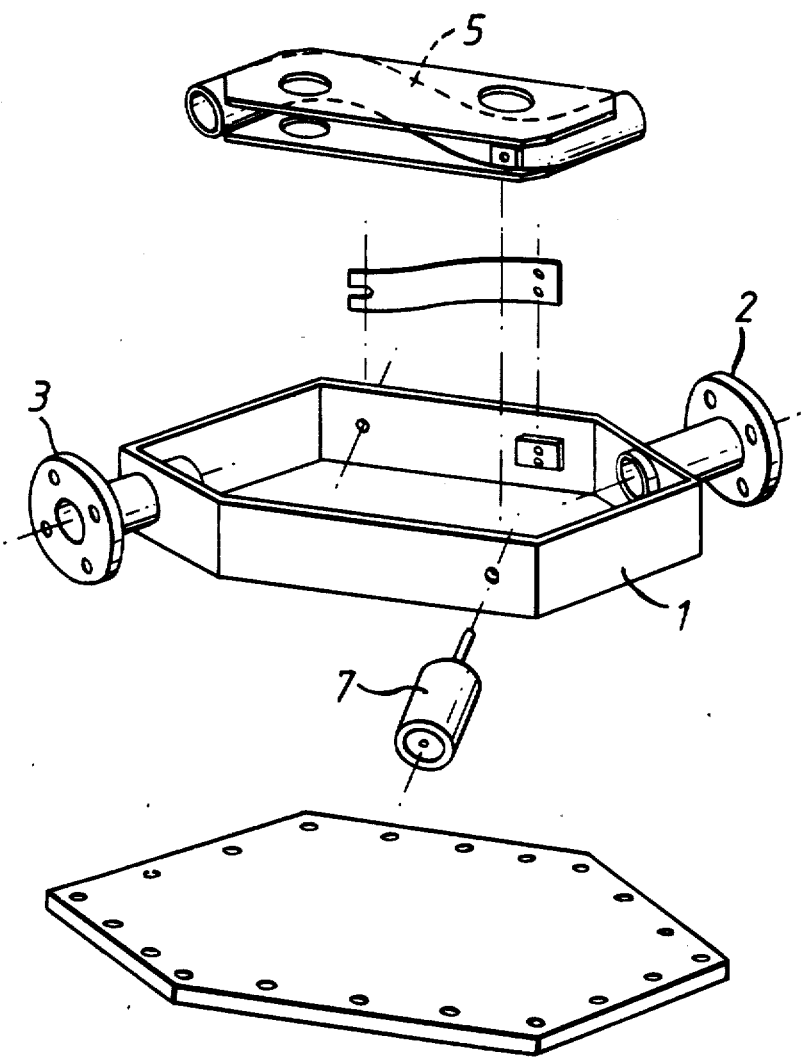
FIG. 2 is an exploded diagram of the flow meter housing.

A plenum chamber or housing 1 has an inlet 2 and an outlet 3 for a fluid. Liquid and gas phase input to the inlet 2 is controlled by valves and measured by sensors 4 to provide the complementary velocity, density or hold up parameters necessary for mass flow calculation. The housing 1 is fabricated from mild steel and forms the main structural element of the assembly. The comparatively massive plenum frame absorbs mechanical loading due to pipe distortion, expansion etc.

A reaction tube 5 having a pair of opposed right angle bends is located within the housing and is located in fluid flow relationship with the inlet and outlet.

The inlet and outlet pipe inner ends are faced off radially to closely fit the ends of the reaction tube. Axial clearances at these points are between 0.5 mm and 1 mm depending on flow direction, the smallest clerance being at the inlet end. The gaps 6 are not sealed, allowing pressure equalisation between tube 5 and housing 6 to take place.

The reaction tube 5 was mounted on a flexure suspension to keep its end axes aligned with the inlet and outlet pipe axes, whilst still allowing free independent axial movement at each end.

The load cells 7 were mounted outside the plenum frame, reaction tube forces being transmitted by probes passing through positive clearance ptfe bushes. The preferred embodiment is with the reaction tube 5 mounted directly onto load cells inside the housing. This eliminates the need for a reaction tube suspension and probes and enables the flow meter to be less complex and more accurate.

The load cells fitted to the flow meter were of the "Pye Ether" UF2-0-101b compression type and an equivalent "Pioden Controls" unit.

The meter assembly was completed by two plenum covers of 12 mm perspex clamped up with soft rubber gaskets to the flange faces of the plenum frame.

The sum of the readings from the loadcells 7 is proportional to the couple generated by the momentum change. Combination of the signal with that from a velocity or other form of sensor gives a continuous mass flow reading, which may be sampled, integrated, or otherwise processed as required.

The difference between the two load cell signals is proportional to the wall friction/turbulence, etc effects of the fluid path. If upstream turbulence is allowed for, combination of the difference signal with velocity and temperature information may give a good continuous bulk viscosity output.

With two-phase flow, forces measured will have high short-term variability, due to individual slugs, etc. It is possible that continuous automatic analysis of characteristic waveforms might be used to identify the type of flow existing, and an estimate of the gas/liquid proportions made. For instance, a high reaction reading relative to the velocity will indicate a high proportion of liquid, and vice versa. For intermittent flow regimes such as slug flow, intensity and ratio of slug to gas might be identifiable.

The reaction tube is rigid and fabricated from erosion and corrosion resistance materials such as ceramics and composites. The reaction tube is suspended on two load cells inside a pressure tight enclosure. This arrangement eliminates or reduces pivot friction.

During use, single or multi phase fluid is passed into the housing through inlet tube 1 into the reaction tube and through the outlet. The fluid also fills the housing allowing pressure equalisation between the tube and the housing to take place.

The change in momentum vector caused by the change of direction of the fluid flow at the bends of the reaction tube results in a turning couple to be set up about the tube midpoint. The signal generated by the load cells is proportional to the instantaneous momentum of fluid passing through the tube. Combination of the load cells signals with those from other sensors enables mass flow to be calculated. The fluid phase hold up measurement is made downstream of the housing/flow tube unit.

I claim:

1. Flow meter comprising a housing having an inlet and an outlet for a fluid, a flow tube located within the housing and allowing fluid from the inlet to the outlet, the flow tube having an S bend geometry comprising a pair of symmetrical bends, one in a first direction and another in an opposite direction, each of said bends having a midpoint, the ends of the flow tube being slightly spaced apart from the respective housing inlet and outlet to enable fluidic communication between the flow tube and the housing, the flow tube being rigidly mounted on means for measuring the reaction forces generated by fluid flow through the flow tube, and said means being disposed normal to the midpoints in the bends of the flow tube.

2. Flow meter according to claim 1 in which there is a narrow circumferential gap or slot between the ends of the flow tube and the respective housing inlet or outlet.

3. Flow meter according to claims 2 or 1 wherein said bends are 90 bends and are disposed in the same plane.

4. Flow meter according to claim 1 in which the fluid flow path at the outlet has the same direction and is parallel to the fluid flow at the inlet.

5. Flow meter according to claim 1 in which the bore of the flow tube is substantially the same as the bores of the housing inlet and outlet.

6. Flow meter according to claim 1 in which the means for measuring generated reaction forces comprises a force transducer or load cell.

7. Flow meter according to claim 6 in which the force transducer or load cell is in the form of a strain gauge or piezo-electric device.

8. Flow meter according to claim 6 or 7 in which the means for measuring generated reaction forces is located between the flow tube and the housing.

* * * * *